US012139503B2

(12) United States Patent
Torgov et al.

(10) Patent No.: US 12,139,503 B2
(45) Date of Patent: Nov. 12, 2024

(54) BORYLATED AMINO ACID COMPOSITIONS FOR USE IN BORON NEUTRON CAPTURE THERAPY AND METHODS THEREOF

(71) Applicant: TAE Life Sciences, Foot Hill Ranch, CA (US)

(72) Inventors: Michael Y. Torgov, Redondo Beach, CA (US); Tioga J. Martin, Los Angeles, CA (US); Arthur B. Raitano, Los Angeles, CA (US)

(73) Assignee: TAE Life Sciences, LLC, Irvine, CA (US)

( * ) Notice: Subject to any disclaimer, the term of this patent is extended or adjusted under 35 U.S.C. 154(b) by 106 days.

(21) Appl. No.: 17/803,382

(22) Filed: Jun. 9, 2022

(65) Prior Publication Data

US 2023/0295190 A1  Sep. 21, 2023

Related U.S. Application Data

(63) Continuation of application No. 16/873,245, filed on Mar. 4, 2020, now Pat. No. 11,566,031.

(51) Int. Cl.
*C07F 5/05* (2006.01)
*A61K 41/00* (2020.01)

(52) U.S. Cl.
CPC ............ *C07F 5/05* (2013.01); *A61K 41/0095* (2013.01)

(58) Field of Classification Search
CPC .................................. A61K 41/00; C07F 5/05
See application file for complete search history.

(56) References Cited

U.S. PATENT DOCUMENTS

| | | | |
|---|---|---|---|
| 6,150,392 | A | 11/2000 | Thomas et al. |
| 8,765,997 | B2 | 7/2014 | Shaw et al. |
| 2013/0131192 | A1 | 5/2013 | Guo et al. |
| 2016/0184271 | A1 | 6/2016 | Lopes Da Silva |
| 2017/0015684 | A1 | 1/2017 | Takenaka et al. |
| 2018/0155368 | A1 | 6/2018 | Li et al. |

FOREIGN PATENT DOCUMENTS

EP  2865682  4/2015

OTHER PUBLICATIONS

Jacek Capala et al., Boron neutron capture therapy for glioblastoma multiforme: clinical studies in Sweden, J Neuro-Oncology, 62, 135-144. (Year: 2003).*
Scalise, et. al., The Human SLC7A5 (LAT1): The Intriguing Histidine/Large Neutral Amino Acid Transporter . . . Frontiers in Chem. vol. 6, Art. 243, pp. 1-12 (Jun. 22, 2018).
Uchino, et. al., Transport of Amino Acid-Related Compounds Mediated by L-Type Amino Acid Transporter 1 (LAT1): Insights into . . . Mol. Pharm. vol. 61, No. 4, pp. 729-737 (2002).
Wongthai, et. al., Boronophenylalanine, a Boron Delivery Agent for Boron Neutron Capture therapy, is Transported by ATB, LAT1 and LAT2, Cancer Sci. 106:3 pp. 279-286 (2015).
Malan, et. al., A Concise Preparation of 4-Borono-L-phenylalanine (L-BPA) from L-phenylalanine, J. Org. Chem., 63 pp. 8019-8020 (1998).
Malan, et. al., Synthesis of 4-borono-L-phenylalanine, Synlett, pp. 167-168 (Feb. 1996).
Nedunchezhian, et. al., Boron Neutron Capture Therapy—A Literature Review, J. Clin. and Diag. Res., vol. 10(12): ZE01-ZE04 (Dec. 2016).
Li, et. al., Decarboxylative borylation, Science 356, eaam7355 (2017).
Futmura, et. al., Evaluation of a Novel Sodium Borocaptate-containing Unnatural Amino Acid as a Boron Delivery Agent for Neutron Capture Therapy . . . , Rad. Onco. (2017) 12:26.
Friesema, et. al., Thyroid Hormone Transport by the Heterodimeric Human System L Amino Acid Transporter, Endrocrinology, 142(10):4339-4348 (Oct. 2001).
Hattori, et. al., Biological Evaluation of Dodecaborate-containing L-Amino Acods for Boron Neutron Capture Therapy, J. Med. Chem. 2012, 55, 6980-6984.
Singh, et. al., Insights into the Structure, Function, and Ligand Discovery of the Large Neutral Amino Acid Transporter 1, LAT1, Int. J. Mol. Sci. (2018), 19, 1278.
Kanai, et. al., Expression Cloning and Characterization of a Transporter for Large Neutral Amino Acids Activated by the Heavy Chain . . . , J. Biol. Chem. (1998), 273:23629-23632.
Matarese, et. al., A.S.P.E.N. Position Paper: Parenteral Nutrition Clutamine Supplementation, Nutr. Clin. Pract. (2011) 26:479.

* cited by examiner

*Primary Examiner* — Michael G. Hartley
*Assistant Examiner* — Jagadishwar R Samala
(74) *Attorney, Agent, or Firm* — LOSMP; Shane M. Popp

(57) ABSTRACT

Borylated Amino Acid ("BAA") compositions and methods of making BAAs are disclosed herein. Consequently, the BAAs can be administered to patients as a Neutron Capture Agent and provide a method of treating cancer, immunological disorders and other disease by utilizing a Neutron Capture Therapy modality.

11 Claims, 14 Drawing Sheets

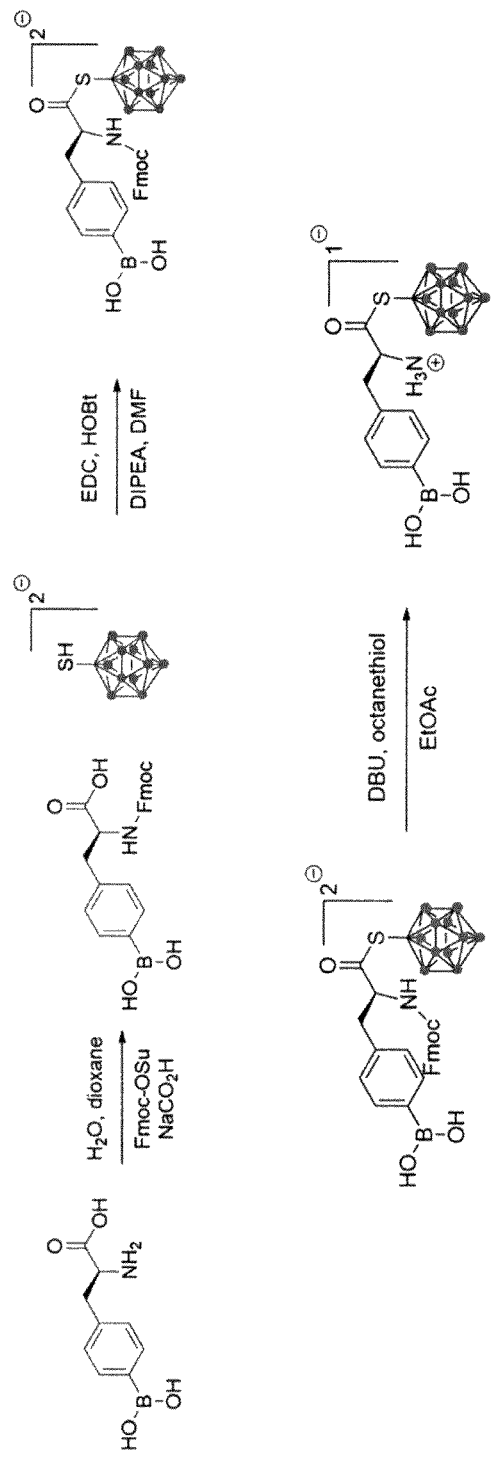
Figure 1. Chemical Synthesis for BPA-BS

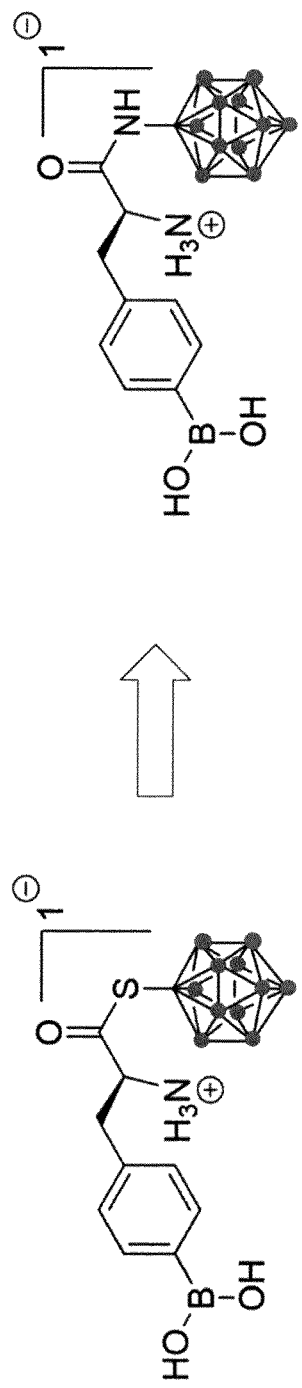
Figure 2. Chemical Synthesis for BPA-BN

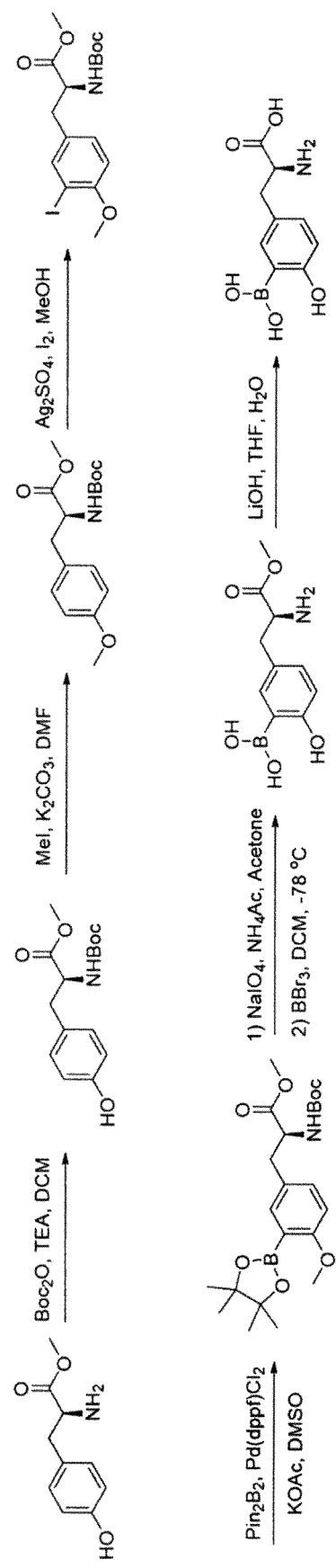
Figure 3. Chemical Synthesis for TLS00192

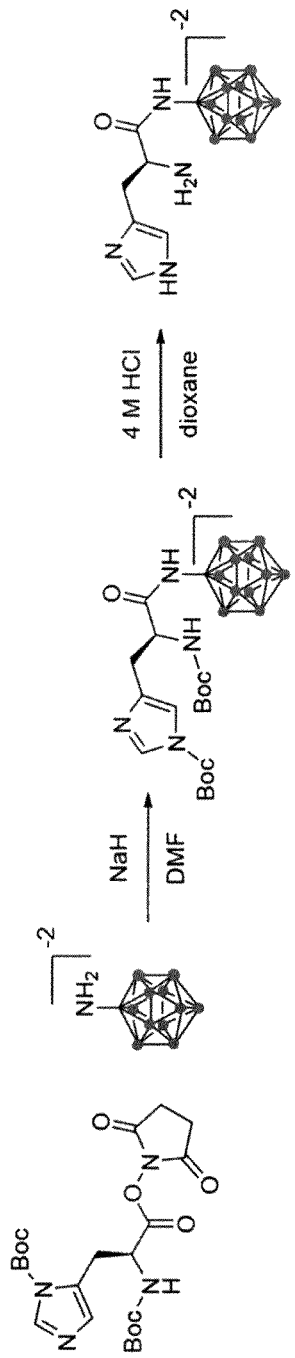
Figure 4. Chemical Synthesis for TLS00178

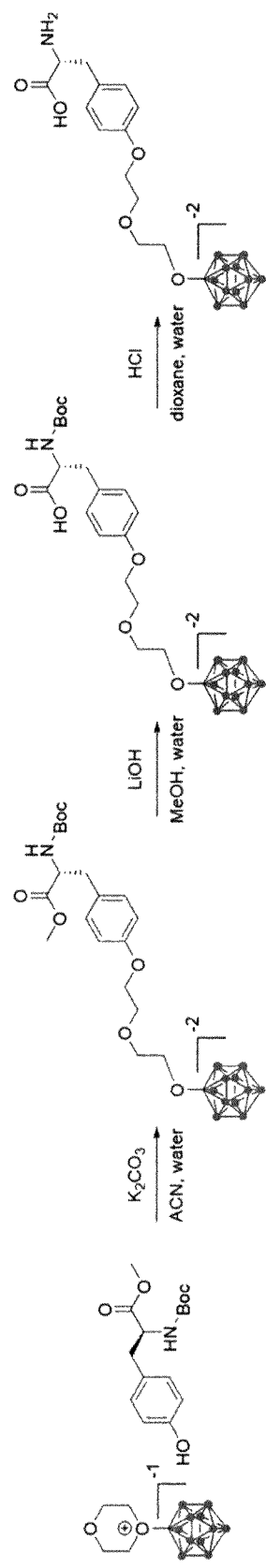
Figure 5. Chemical Synthesis for TLS00190

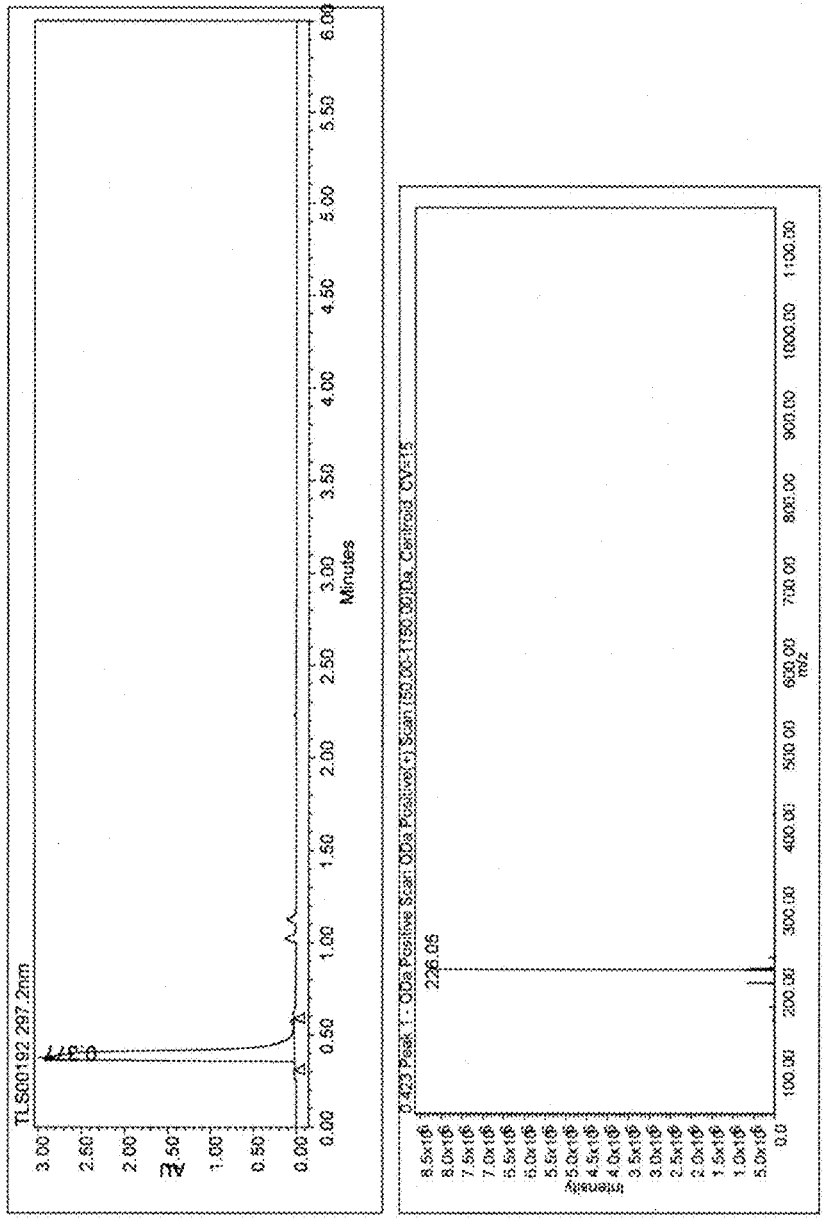
Figure 6. LSMC Purity and Mass Confirmation of TLS00192

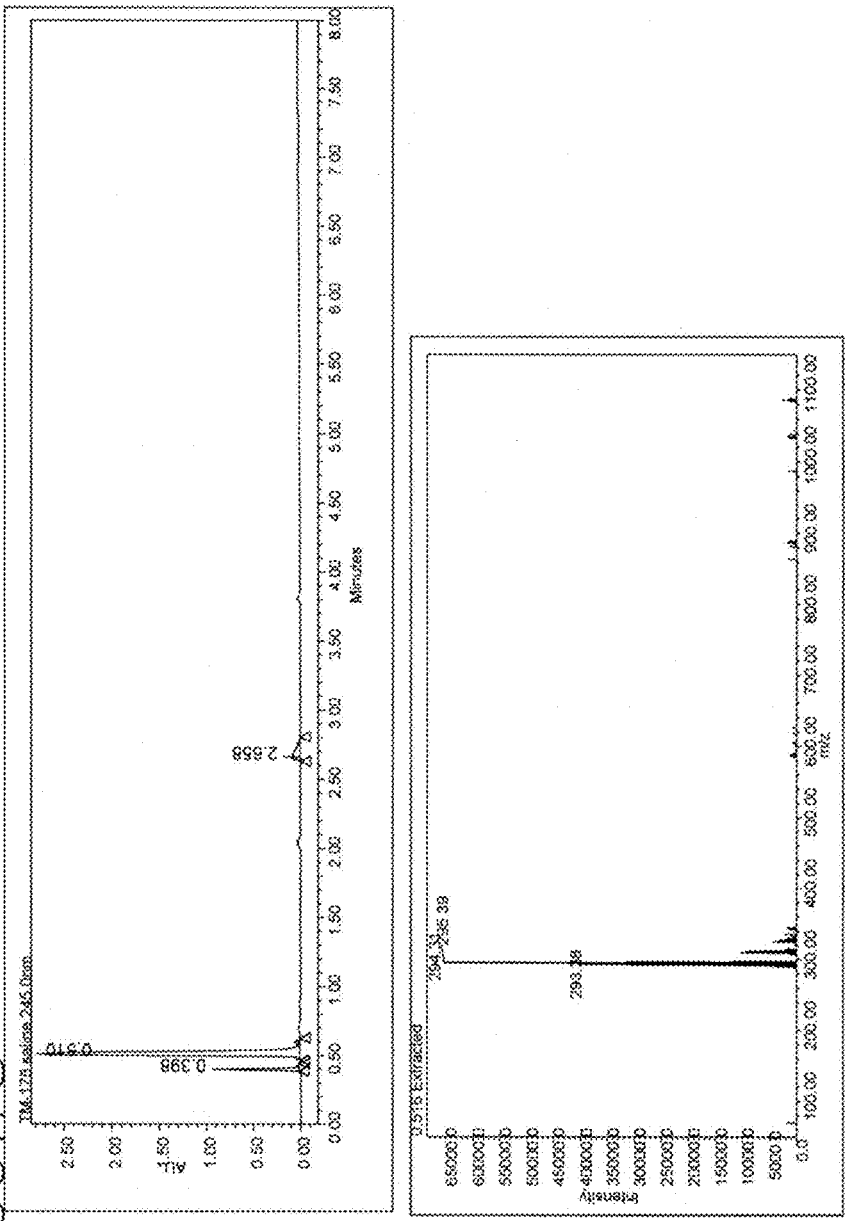
Figure 7. LSMC Purity and Mass Confirmation of TLS00178

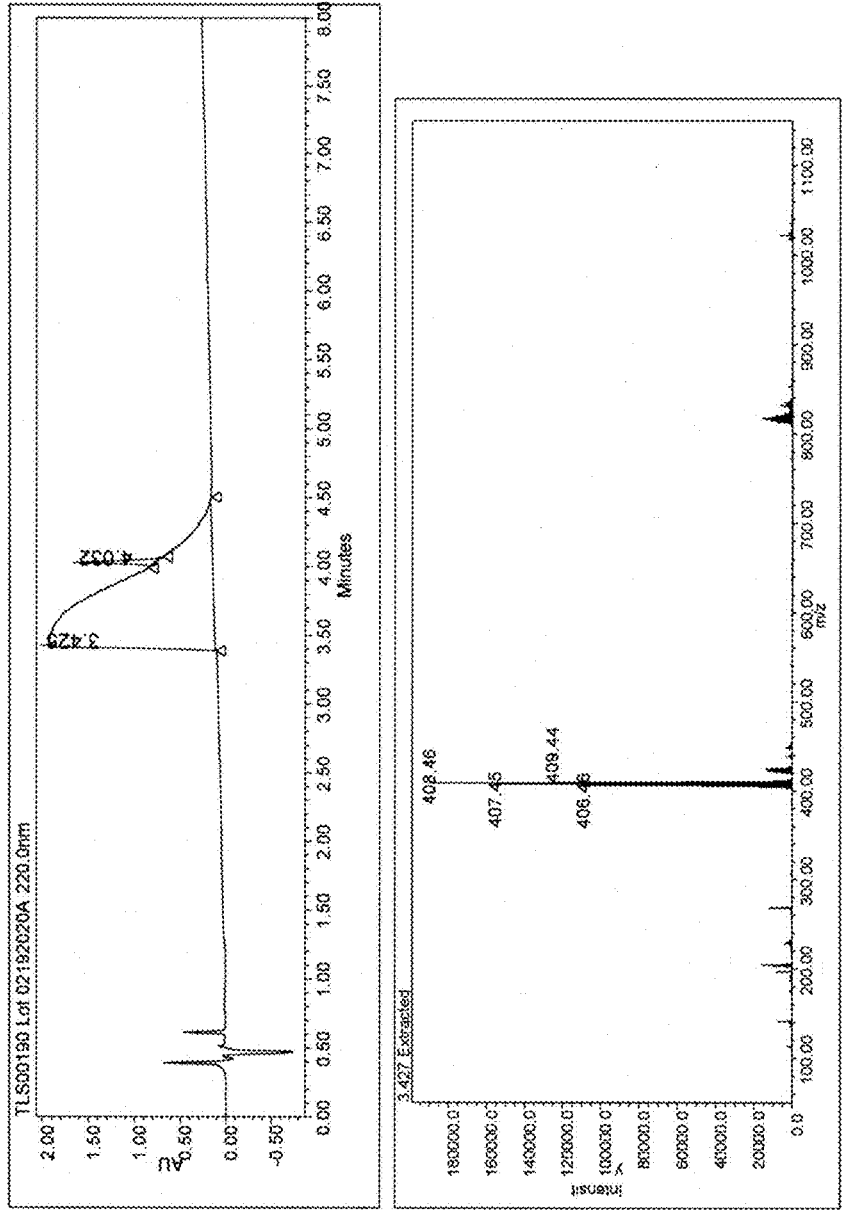
Figure 8. LSMC Purity and Mass Confirmation of TLS00190

Figure 9. LSMC Purity and Mass Confirmation Summary

| Line | Compound | Purity by LC, % | Expected Mass, Da | Observed Mass, Da | Ionization Mode |
|---|---|---|---|---|---|
| 1 | TLS00178 | 93.0% | 294 | 295.3 [M-H$^+$] | Negative |
| 2 | TLS00190 | 98% | 409.0 | 408.4 [M-H$^+$] | Negative |
| 3 | TLS00192 | 100%[1] | 225.0 | 226.05 [M+H$^+$] | Positive |

[1]The amount of the L-tyrosine starting material is 4-7% by proton NMR

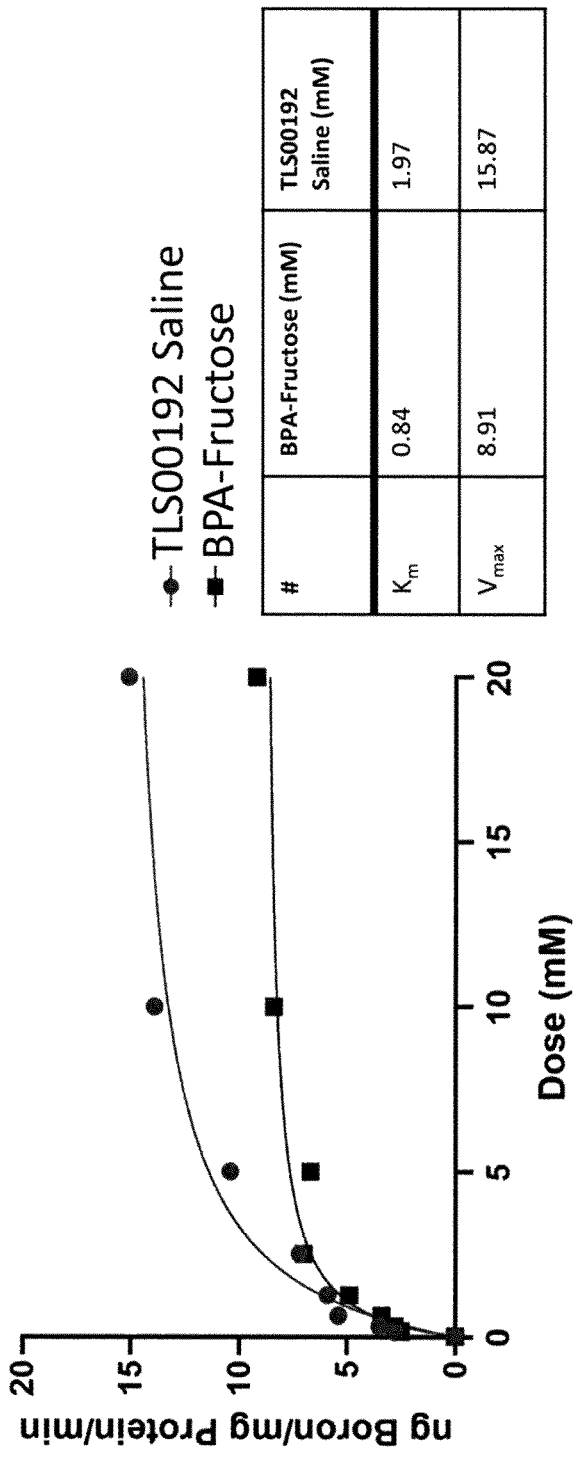
Figure 10. Kinetic Parameters of TLS00192 and BPA-Fructose

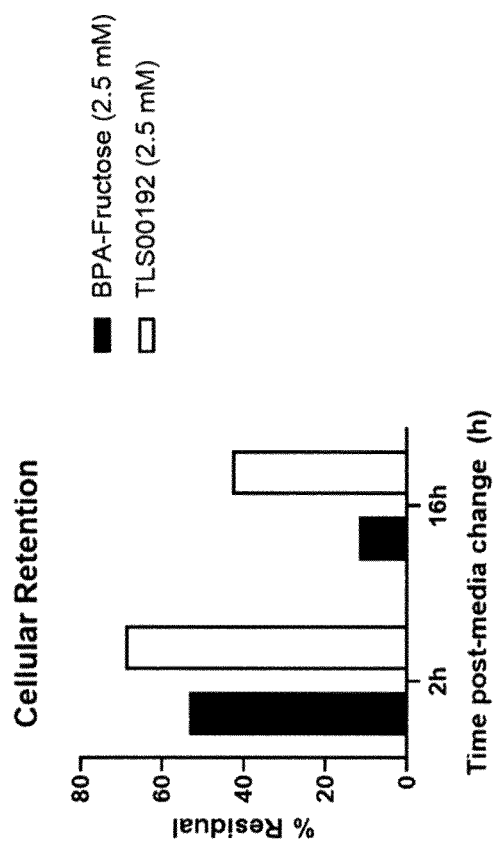
Figure 11. Cellular Retention of TLS00192 and BPA-Fructose in FaDu cells

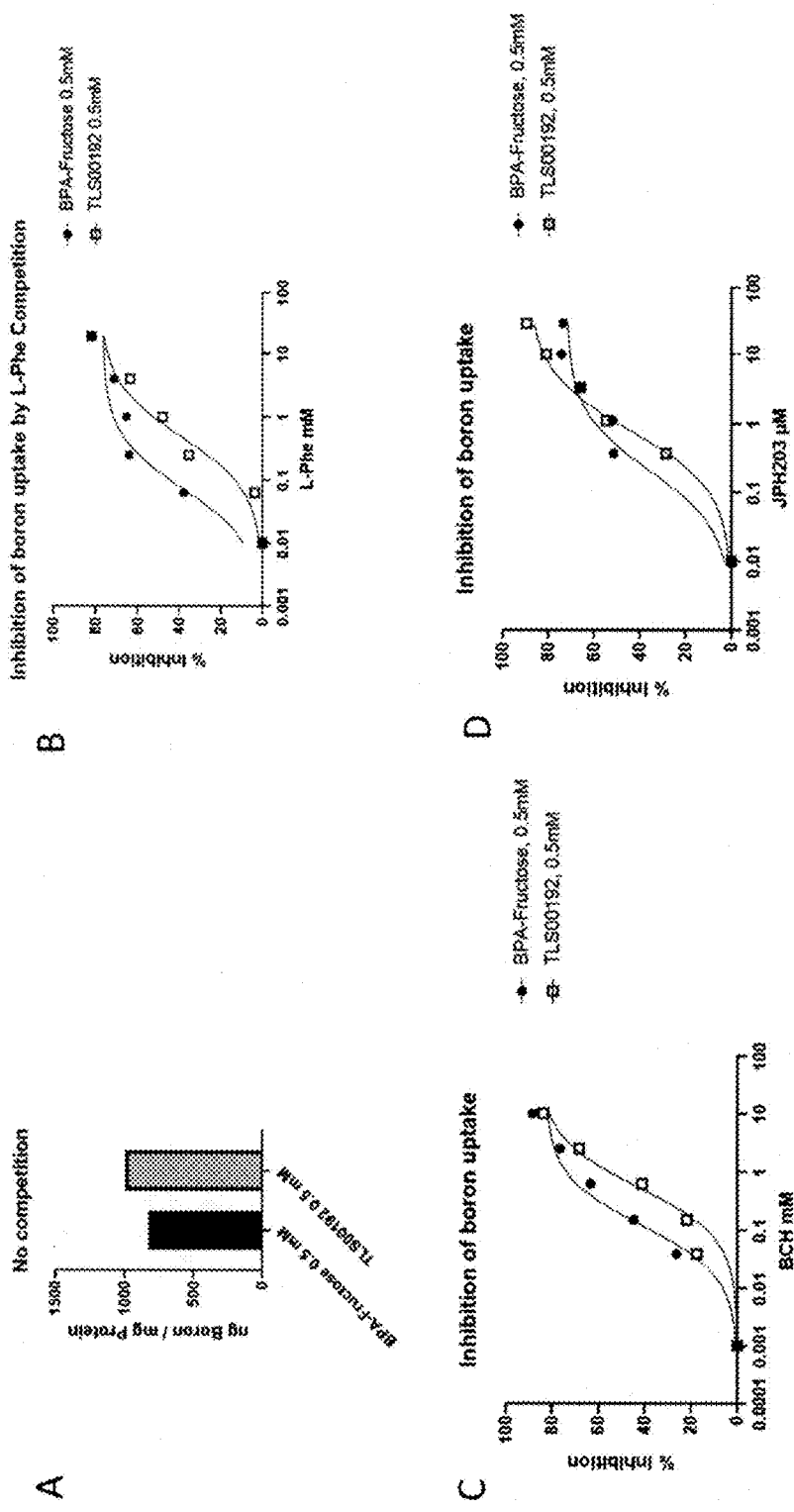
Figure 12. LAT-1 Mediated Competition Studies for TLS00192

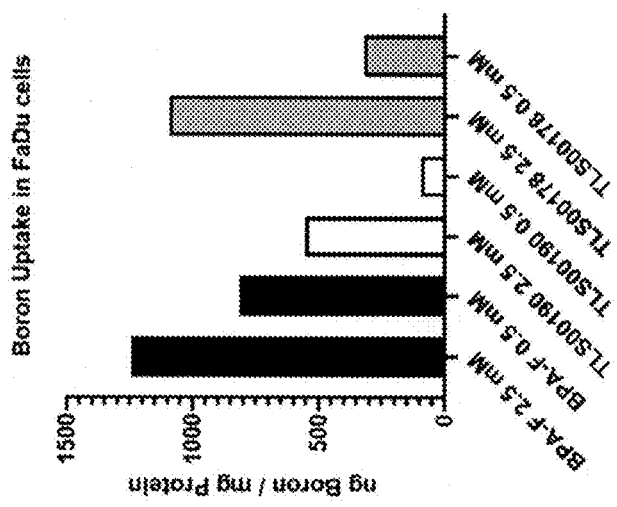
Figure 13. Boron Uptake TLS00190 and TLS00178 in FaDu Cells

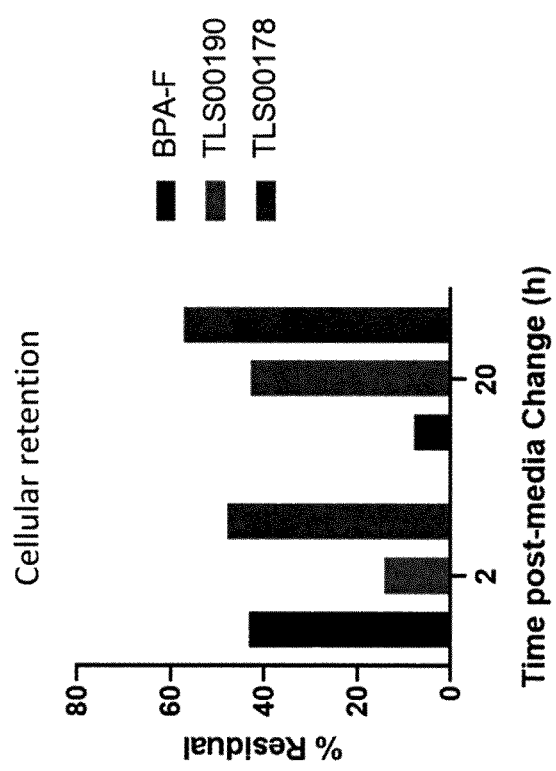
Figure 14. Cellular Retention of TLS00190, TLS00178 and BPA-Fructose in FaDu cells

BORYLATED AMINO ACID COMPOSITIONS FOR USE IN BORON NEUTRON CAPTURE THERAPY AND METHODS THEREOF

CROSS-REFERENCE TO RELATED APPLICATIONS

This application is a continuation of U.S. Ser. No. 16/873,245, filed 4 Mar. 2020, which claims priority to U.S. Provisional Patent Application No. 62/919,156 filed 4 Mar. 2019, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to the field of boron neutron capture therapy (BNCT). Specifically, the invention relates to borylated amino acid ("BAA") or ("BAAs") compositions which can be used as a vehicle for neutron capture therapy in humans. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasise to sites distant from the primary tumor and with very few exceptions, metastatic disease fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neckand lung adenocarcinoma) which are sometimes limited to standard radiotherapy and/or chemotherapy. Nonetheless, detrimental effects of these therapies are chemo- and radioresistance, which promote loco-regional recurrences, distant metastases and second primary tumors, in addition to severe side-effects that reduce the patients' quality of life.

Neutron Capture Therapy (NCT) is a promising form of radiation therapy. It is a technique that selectively kills tumor cells using boron compound while sparing the normal cells. BNCT relies on the propensity of non-radioactive $^{10}B$ isotope to absorb epithermal neutrons that fall into the low energy range of 0.5 keV<$E_n$<30 keV. Following neutron capture, boron atom undergoes a nuclear fission reaction giving rise to an alpha-particle and a recoiled lithium nucleus ($^7Li$) as follows:

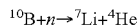

$$^{10}B+n \rightarrow {}^7Li + {}^4He$$

The alpha particle deposits high energy i.e. 150 keV/μm along their short path eseentially restricted to a sigle cell diameter that results in a double strand DNA breaks followed by cancer cell death by apoptosis. Thus BNCT integrates a concept of both chemotherapy, targeted therapy and the gross anatomical localization of traditional radiotherapy.

Even though the conceptual techniques of NCT and specifically Boron Neutron Capture Thereapy (BNCT) are well known, the technological limitations associated with this type of treatment have slowed progress. During the early investigations using the research reactors of MIT in 1960's, several dosens of patients were treated using disodium decahydrodecaborate, which was considered less toxic than simple boron compounds used previously yet capable of delivering more boron to the cell. Unfortunately, BNCT studies were halted in the USA due to the severe brain necrosis in the patients undergoing BNCT and the potential harm of using nuclear reactors.

Hiroshi Hatanaka in 1968 re-investigated clinical application of BNCT in Japan using sodium borocaptate (BSH) by directing the beam to surgically exposed intracranial tumor and reported of achieving 58% of 5-year survival rate. In 1987 clinicians in Japan applied BNCT for the treatment of malignant melanoma using boronophenylalanine (BPA) as boron compound. Thus, slow resurgence of BNCT took place albeit limited to the countries with an access to research reactor facilities capable of delivering epithermal neutron beam. Currently, given the technological improvements in both (i) the infusion and delivery of a capture compound, which preferably concentrates in the tumor, and (ii) more abundant and easier access to neutron beam using cyclotrons, there has been a resurgence in NCT treatment methods.

The proton boron fusion reaction relies on the naturally abundant $^{11}B$ isotope rather than $^{10}B$ required for BNCT. Unlike BNCT, three alpha particles are emitted after the fusion reaction between a proton ($^1H$) and a boron ($^{11}B$) nucleus: $p+{}^{11}B \rightarrow 3\alpha$. The proton beam has the advantage of a Bragg-peak characteristic reducing the normal tissue damage and when combined with proton capture, may improve the efficacy of the proton therapy alone.

Carriers of boron have evolved since 1950s and are reviewed in NEDUNCHEZHIAN, et. al., J. Clin. Diag. Res., vol. 10 (12) (December 2016). Briefly, the $1^{st}$ generations of boron compounds represented by boric acid and its derivatives were either toxic or suffered from low tumor accumulation/retention. BPA and BSH are both considered the $2^{nd}$ generation compounds that emerged in 1960s. These had significantly lower toxicity and better PK and biodistribution. BPA-fructose complex is considered the $3^{rd}$ generation compound that is used to treat patients with H&N, glioblastoma and melanoma using BNCT since 1994. BPA-fructose and BSH are the only compounds that are being used in clinic as boron carriers to date although both low and high molecular weight biomolecules such as nucleosides, porphyrins, liposomes, nanoparticles and mAbs have been evaluated for the tumor targeting in preclinical models. The main deficiency of BPA-fructose is relatively low solubility combined with its rapid clearance that prevents achieving high Cmax in blood, one of the drivers influencing the tumor uptake.

From the aforementioned, it will be readily apparent to those skilled in the art that a new treatment paradigm is needed in the treatment of cancers and immunological diseases. By using modern chemical synthesis and modifying natural amino acids with boron, a new disease treatment can be achieved with the overall goal of more effective treatment, reduced side effects, and lower production costs.

Given the current deficiencies associated with NCT, it is an object of the present invention to provide new and improved methods of treating cancer(s), immunological disorders, and other diseases utilizing borylated amino acids and NCT.

SUMMARY OF THE INVENTION

The invention provides for compositions comprising natural amino acids which have been borylated via chemical synthesis for use as a delivery modality to treat human diseases such as cancer, immunological disorders, including but not limited to rheumatoid arthritis, ankylosing spondylitis, and other cellular diseases, including but not limited to Alzheimer's disease. In certain embodiments, the borylated amino acids are comprised of naturally occurring amino acids such as phenylalanine, tryptophan, tyrosine, histidine, and any other naturally occurring amino acid set forth in Table I.

In a further embodiment, the invention comprises methods of concentrating Boron in a cell comprising (i) synthesizing a borylated amino acid ("BAA"); (ii) administrering the BAA to a patient, and (iii) irradiating the cell with neutrons.

In another embodiment, the present disclosure teaches methods of synthesizing BAA's.

In another embodiment, the present disclosure teaches methods of treating cancer(s), immunological disorders and other diseases in humans.

BRIEF DESCRIPTION OF THE FIGURES

FIG. 1. Chemical Synthesis for BPA-BS.
FIG. 2. Chemical Synthesis for BPA-BN.
FIG. 3. Chemical Synthesis for TLS00192.
FIG. 4. Chemical Synthesis for TLS00178.
FIG. 5. Chemical Synthesis for TLS00190.
FIG. 6. LCMS Purity and Mass Confirmation of TLS00192.
FIG. 7. LCMS Purity and Mass Confirmation of TLS00178.
FIG. 8. LCMS Purity and Mass Confirmation of TLS00190.
FIG. 9. LCMS Purity and Mass Confirmation of Summary.
FIG. 10. Kinetic Parameters of TLS00192 and BPA-Fructose.
FIG. 11. Cellular Retention of TLS00192 and BPA-Fructose in FaDu cells.
FIG. 12. LAT-1 Mediated Competition Studies for TLS00192.
FIG. 13. Boron Uptake of TLS00190 and TLS00178 in FaDu Cells.
FIG. 14. Cellular Retention of TLS00190, TLS00178, and BPA-Fructose in FaDu Cells.

DETAILED DESCRIPTION OF THE INVENTION

Outline of Sections
  I.) Definitions
  II.) BPA
  III.) BSH
  IV.) Boron
    a. Boron Generally
  V.) Naturally Occurring Amino Acids
  VI.) Borylated Amino Acids (BAAs)
    a. BPA-BS
    b. BPA-BN
    c. Amino Acid Composition(s)
    d. BAA Comprising Phenylalanine
    e. BAA Comprising Tryptophan
    f. BAA Comprising Tyrosine
    g. BAA Comprising Histidine
  VII.) Boron Neutron Capture Therapy Using BAAs
  VIII.) Proton Boron Fusion Therapy Using BAAs
  IX.) Methods of Delivering BAAs to a Cell
  X.) KITS/Articles of Manufacture I.) Definitions:

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to, represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

"Amino Acid" means a simple organic compound containing both a carboxyl (—COOH) and an amino (—NH$_2$) group.

"Borylation" means reactions that produce an organoboron compound through functionalization of aliphatic and aromatic C—H bonds.

"Borylated Amino Acid" (BAA) means a compound comprising a naturally occurring amino acid, such as those set forth in Table I, which has undergone a borylation reaction. BAAs can be synthesized in multiple formats depending on the underlying amino acid that is being used.

The term "compound" refers to and encompasses the chemical compound (e.g. a BAA) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above The terms "inhibit" or "inhibition of" as used herein means to reduce by a measurable amount, or to prevent entirely.

The term "mammal" refers to any organism classified as a mammal, including mice, rats, rabbits, dogs, cats, cows, horses and humans. In, one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+ under the TNM system.

"Molecular recognition" means a chemical event in which a host molecule is able to form a complex with a second molecule (i.e. the guest). This process occurs through non-covalent chemical bonds, including but not limited to, hydrogen bonding, hydrophobic interactions, ionic interaction.

"Pharmaceutically acceptable" refers to a non-toxic, inert, and/or composition that is physiologically compatible with humans or other mammals.

The term "neutron capture agent" means a stable non-reactive chemical isotope which, when activated by neutrons produces alpha particles.

The term "neutron capture therapy" means a noninvasive therapeutic modality for treating locally invasive malignant tumors such as primary brain tumors and recurrent head and neck cancer and other immunological disorders and disease by irradiating a neutron capture agent with neutrons.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

II.) BPA

By way of reference, ($^{10}$B)-BPA, L-BPA, or 4-Borono-L-phenylalanine (Sigma Aldrich, St. Louis, MO) is a synthetic compound with the chemical formula $C_9H_{12}BNO_4$. The structure is shown below:

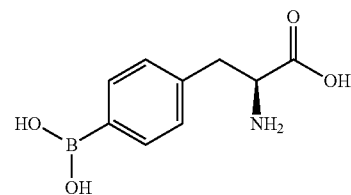

and is an important boronated compound useful in the treatment of cancer though BNCT. It is a widely known compound which many synthesis have been developed (See, U.S. Pat. No. 8,765,997, Taiwan Biotech Co, Ltd., Taoyuan Hsein, Taiwan, and US2017/0015684, Stella Pharma Corp., Osaka Prefecture Univ., Osaka, Japan).

III.) BSH

In addition, BSH, or sodium borocaptate, or BSH sodium borocaptate, or Borocaptate sodium $^{10}$B, or undecahydro-dodecaborane thiol is a synthetic chemical compound with the chemical formula $Na_2B_{12}H_{11}SH$. The structure is shown below:

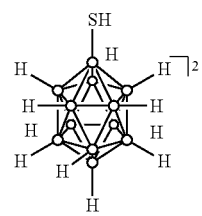

where boron atoms are represented by dots in the vertices for the icosahedron. BSH is used as a capture agent in BNCT. Generally speaking, BSH is injected into a vein and becomes concentrated in tumor cells. The patient then receives radiation treatment with atomic particles called neutrons. The neutrons fuse with the boron nuclei in BSH and to produce high energy alpha particles that kill the tumor cells.

IV.) Boron (a.) Boron Generally

Generally speaking and for purposes of this disclosure, Boron is a chemical element with symbol B and atomic number 5. Primarily used in chemical compounds, natural boron is composed of two stable isotopes, once of which is Boron-10 and the other is Boron-11. Boron-10 isotope is useful for capturing epithermal neutrons, which makes it a promising tool in a therapeutic context using Boron Neutron Capture Therapy. Biologically, the borylated compounds disclosed herein are nontoxic to humans and animals. Based on the foregoing, it will be readily apparent to one of skill in the art that improved modalities for providing high concentrations of boron into a cancer cell are advantagous. It is an object of the present disclosure to provide that advantage.

V.) Naturally Occurring Amino Acids

Generally speaking and for the purposes of this disclosure, naturally occurring amino acids are organic compounds containing amine (—$NH_2$) and carboxyl (—COOH) functional groups, along with a side chain (R group) specific to each amino acid. The key elements of an amino acid are carbon (C), hydrogen (H), oxygen (O), and nitrogen (N), although other elements are found in the side chains of certain amino acids. About 500 naturally occurring amino acids are known (though only 20 appear in the genetic code (Table I)) and can be classified in many ways. They can be classified according to the core structural functional groups' locations as alpha- (α-), beta- (β-), gamma- (γ-) or delta- (δ-) amino acids; other categories relate to polarity, pH level, and side chain group type (aliphatic, acyclic, aromatic, containing hydroxyl or sulfur, etc.). In the form of proteins, amino acid residues form the second-largest component (water is the largest) of human muscles and other tissues. Beyond their role as residues in proteins, amino acids participate in a number of processes such as neurotransmitter transport and biosynthesis.

The twenty (20) amino acids encoded directly by the genetic code (See, Table I) can be divided into several groups based on their properties. Important factors are charge, hydrophilicity or hydrophobicity, size, and functional groups. These properties are important for protein structure and protein-protein interactions. The water-soluble proteins tend to have their hydrophobic residues (Leu, Ile, Val, Phe, and Trp) buried in the middle of the protein, whereas hydrophilic side chains are exposed to the aqueous solvent.

The integral membrane proteins tend to have outer rings of exposed hydrophobic amino acids that anchor them into the lipid bilayer. In the case part-way between these two extremes, some peripheral membrane proteins have a patch of hydrophobic amino acids on their surface that locks onto the membrane. In similar fashion, proteins that have to bind to positively charged molecules have surfaces rich with negatively charged amino acids like glutamate and aspartate, while proteins binding to negatively charged molecules have surfaces rich with positively charged chains like lysine and arginine. There are different hydrophobicity scales of amino acid residues.

Some amino acids have special properties such as cysteine, that can form covalent disulfide bonds to other cysteine residues, proline that forms a cycle to the polypeptide backbone, and glycine that is more flexible than other amino acids.

VI.) Borylated Amino Acids (BAAs)

By way of brief introduction and to better understand the background to the inventive endeavor of the present disclosure, the large neutral amino acid transporter 1 (LAT-1, SLC7a5) is a sodium- and pH-independent transporter, which supplies essential amino acids (e.g., leucine, phenylalanine) to cells. The functional transporter is a heterodimeric disulfide-linked complex composed of the multi-transmembrane subunit SLC7a5 and single transmembrane subunit SLC3a2 (CD98). LAT-1 is the main transporter to channel essential amino acids across such compartments such as the placenta or blood-brain barrier. In addition, LAT-1 also transports the thyroid hormones T3 and T4 (See, FRIESEMA, et al., Endocrinology, 142 (10): 4339-4348 (2001)), the dopamine precursor L-DOPA, as well as amino acid-related exogenous compounds, such as the drugs melphalan and gabapentin (See, UCHINO, et al., Mol. Pharmacol 61:729-737 (2002)). Moreover, its expression is highly upregulated in various types of human cancer that are characterized by an intense demand for amino acids for metabolism and growth (See, SINGH, et. al., Int. J. Mol. Sci. 2018, 19, 1278). Furthermore, it has been reported that the nature of the amino acid side chain influences selectivity of LAT-1 for various amino acids, with the following order in terms of increasing rate of transport: Phe>Trp>Leu>Ile>Met>His>Tyr>Val (See, KANAI, et al., J. Biol. Chem., vol. 273, No. 37, pp. 23629-23632 (1998)). However, the influence of boron addition modification to amino acids is unknown in the art and this disclosure represents a pioneering breakthrough.

The therapeutic potential of BNCT as an effective cancer treatment rests in the selective accumulation of a sufficient amount of $^{10}B$ within cancer cells.

Based on the foregoing, those of ordinary skill in the art have shown that essential amino acid transporter proteins such as LAT1 are responsible for the uptake of certain naturally occurring amino acids. See, SCALISE, et. al., Frontiers in Chem., Vol. 6, Art. 243 (June 2018). With this principle in mind, the present disclosure contemplates the synthesis of naturally occurring amino acids through borylayion reactions to create Borylated Amino Acids ("BAAs") with tumor seeking and tumor localizing properties for use as neutron capture agent in Boron Neutron Capture Therapy ("BNCT") and/or Boron Proton Capture Therapy commonly known as Proton Boron Fusion Therapy ("PBFT"). See, for example, HATTORI, et. al., J. Med. Chem., 55, 6980-6984 (2012).

(a) BPA-thioundecahydro-dodecaborane, i.e. BPA-BS

In one embodiment, a precursor composition with the following formula is within the scope of the of the present disclosure:

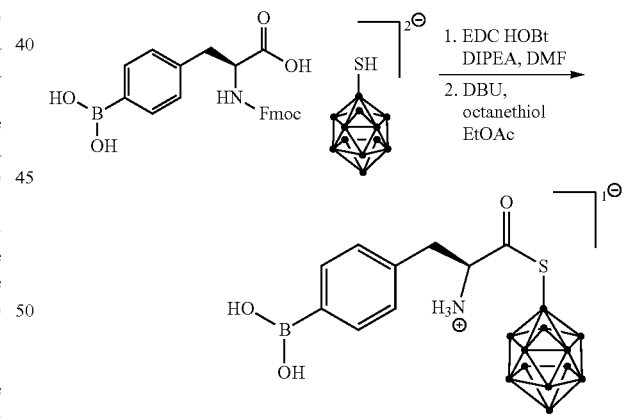

It will be appreciated by one of ordinary skill in the art that the above composition is a precursor for more complex branched BAAs using additional naturally occurring amino acids, such as phenylalanine, trypophan, tyrosine, and/or histidine. The synthesis of BPA-BS shown in FIG. 1. can be achieved through peptide coupling conditions using Fmoc pretected BPA, followed by deprotection to reveal the target material.

(b) BPA-aminoundecahydrododecaborane, i.e. BPA-BN

In one embodiment, a second precursor composition with the following formula is within the scope of the of the present disclosure:

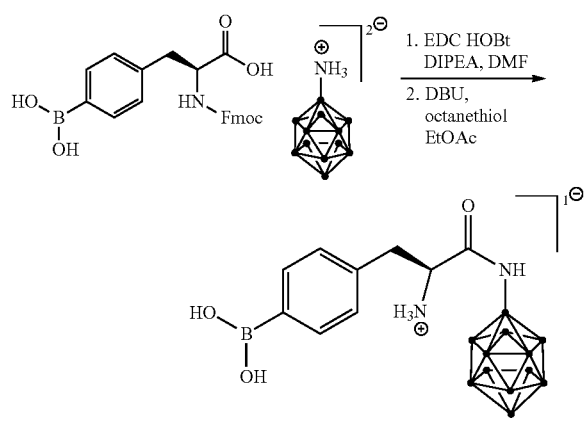

It will be appreciated by one of ordinary skill in the art that BPA-BN precursor is a modification of BPA-BS and is a further precursor for more complex branched BAAs using additional naturally occurring amino acids, such as Phenylalanine, Tryptophan, Tyrosine, and/or Histidine. The synthesis takes place as shown in FIG. 2. For further reference, see, KIRIHATA, et. al., 18$^{th}$ International BNCT Conference, Taipei (October 2018). The synthesis of these compounds can be achieved through peptide coupling between Fmoc-pretected BPA and ammonia undecahydrododecaborate followed by deprotection to reveal the target material.

Utilizing the precursors of the present disclosure, BAA's which have a functional uptake in certain complexes can be synthesized to deliver concentrated amounts of boron to a cancer or otherwise diseased cell for use in BNCT and/or other cancer treatment modalities. For purposes of this disclosure, in one embodiment, the amino acid comprises valine, leucine, isoleucine, histidine, trypophan, tyrosine, and any amino acid set for in Table I.

The principle can be achieved through side chain manipulations, peptide couplings, and decarboxylation-borolation. See, LI, et. al., Science 356, 1045 (2017); Synlett 1996 (02): 167-168; and US2018/0155368 (Neuboron Medtech, Nanjing, China). The wide diversity of useful reactivity that is specific to boronic acids such as cross-coupling, oxidation, amination, and homologation is shown to guide retrosynthetic analysis. Also contemplated in the present disclosure is the manipulation of solubility and lipophilicity through the use of boronic esters in lieu of acid. Subsequent to the modification(s) disclosed herein, additional antigen complexes and transporters may be implicated through selective borolation of their respective molecular substrates.

(c) Amino Acid Composition(s)

In one embodiment, a BAA with the following formula is within the scope of the of the present disclosure ("Phenylalanine derivatives"):

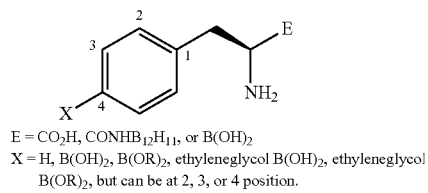

E = CO$_2$H, CONHB$_{12}$H$_{11}$, or B(OH)$_2$
X = H, B(OH)$_2$, B(OR)$_2$, ethyleneglycol B(OH)$_2$, ethyleneglycol B(OR)$_2$, but can be at 2, 3, or 4 position.

Where E=CO$_2$H, CONHB$_{12}$H$_{11}$, B(OH)$_2$; and
X=H, B(OH)$_2$, Bpin, (—O—CH$_2$CH$_2$)$_2$—O—B$_{12}$H$_{11}$.

In a further embodiment, a BAA with with the following formula is within the scope of the of the present disclosure ("Histidine derivatives"):

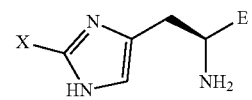

E = CO$_2$H, CONHB$_{12}$H$_{11}$, or B(OH)$_2$
X = H, B(OH)$_2$, B(OR)$_2$, ethyleneglycol B(OH)$_2$, ethyleneglycol B(OR)$_2$, Where E=CO$_2$H, CONHB$_{12}$H$_{11}$, B(OH)$_2$; and
X=H, B(OH)$_2$, Bpin, (—O—CH$_2$CH$_2$)$_2$—O—B$_{12}$H$_{11}$.

In a further embodiment, a BAA with with the following formula is within the scope of the of the present disclosure ("Tyrosine derivatives"):

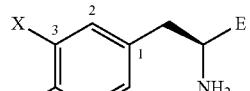

E = CO$_2$H, CONHB$_{12}$H$_{11}$, or B(OH)$_2$
X = H, B(OH)$_2$, B(OR)$_2$, ethyleneglycol B(OH)$_2$, ethyleneglycol B(OR)$_2$, but can be at carbon 2 or 3.

Where E=CO$_2$H, CONHB$_{12}$H$_{11}$, B(OH)$_2$; and
X=H, B(OH)$_2$, Bpin, (—O—CH$_2$CH$_2$)$_2$—O—B$_{12}$H$_{11}$.

In a further embodiment, a BAA with with the following formula is within the scope of the of the present disclosure:

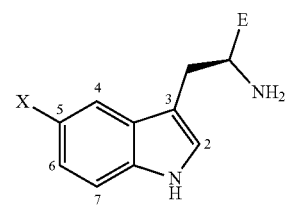

E = CO2H, CONHB$_{12}$H$_{11}$, or B(OH)2
X = H, B(OH)2, B(OR)$_2$, ethyleneglycol B(OH)2, ethyleneglycol B(OR)$_2$, but can be at 2, 4, 5, 6, or 7 position (d) BAA Comprising Phenylalanine Phenylalanine is an essential amino acid with the following chemical formula:

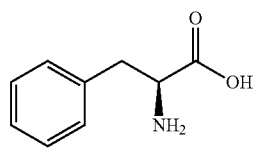 [SMILES: N[C@@H](Cc1ccccc1)C(=O)O]

and is the precursor of the amino acid tyrosine. Phenylalanine is highly concentrated in the human brain and plasma. High plasma concentrations of phenylalanine influence the blood-brain barrier transport of large neutral amino acids. The high plasma phenylalanine concentrations increase phenylalanine entry into the brain and restrict the entry of other large neutral amino acids. Phenylalanine has been found to interfere with different cerebral enzyme systems. Phenylalanine is better absorbed than tyrosine and has been known to cause cause fewer headaches. Certain cancers have been known to use more phenylalanine that other types of cancer. For example, melanomas have been shown to utilize higher concentrations of phenylalanine.

Accordingly, the utilization of borylated phenylalanine as a neutron capture agent in certain cancers is contemplated by the present disclosure.

In one embodiment of the present disclosure, a BAA comprising phelyalanine has the following chemical formula:

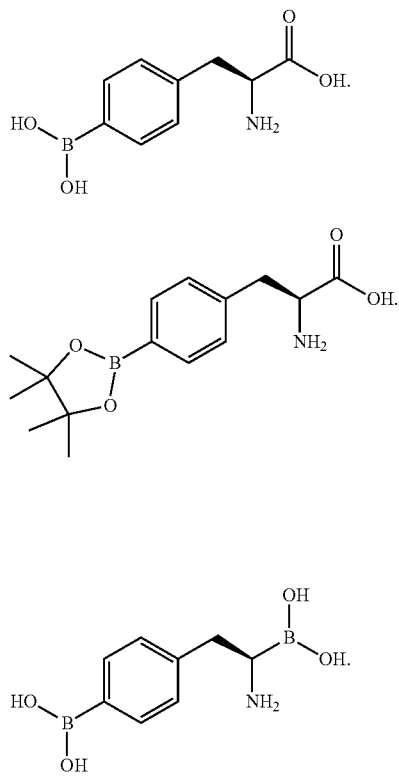

Note, the dots in the Structure No. IV repreent BH. The black dot at one vertex represents B. The B12H11 cluster has net charge of −2.

(e) BAA Comprising Tryptophan

Tryptophan is an essential amino acid with the following chemical formula:

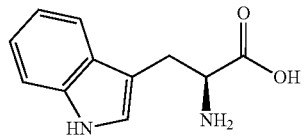 [SMILES: N[C@@H](Cc1c[nH]c2ccccc12)C(=O)O]

and is the precursor of both serotonin and melatonin. Melatonin is a hormone that is produced by the pineal gland inmammals, which regulates sleep and wakefulness. Serotonin is a brain neurotransmitter, platelet clotting factor, and neurohormone found in organs throughout the body. There are a number of conditions or diseases that are characterized tryptophan deficiencies.

For instance, fructose malabsorption causes improper absorption of tryptophan in the intestine, which reduces levels of tryptophan in the blood and leads to depression. High corn or other tryptophan-deficient diets can cause pellagra, which is a niacin-tryptophan deficiency disease with symptoms of dermatitis, diarrhea, and dementia. Hartnup's disease is a disorder in which tryptophan and other amino acids are not absorbed properly. Symptoms of Hartnup's disease include skin rashes, difficulty coordinating movements (cerebellar ataxia), and psychiatric symptoms such as depression or psychosis. Tryptophan plays a role in "feast-induced" drowsiness. Ingestion of a meal rich in carbohydrates triggers the release of insulin. Insulin, in turn, stimulates the uptake of large neutral branched-chain amino acids (BCAAs) into muscle, increasing the ratio of tryptophan to BCAA in the bloodstream. The increased tryptophan ratio reduces competition at the large neutral amino acid transporter (which transports both BCAAs and tryptophan), resulting in greater uptake of tryptophan across the blood-brain barrier into the cerebrospinal fluid (CSF). Once in the CSF, tryptophan is converted into serotonin and the resulting serotonin is further metabolized into melatonin by the pineal gland, which promotes sleep.

Accordingly, the utilization of borylated tryptophan as a neutron capture agent in certain cancers is contemplated by the present disclosure.

In one embodiment of the present disclosure, a BAA comprising tryptophan has the following chemical formula:

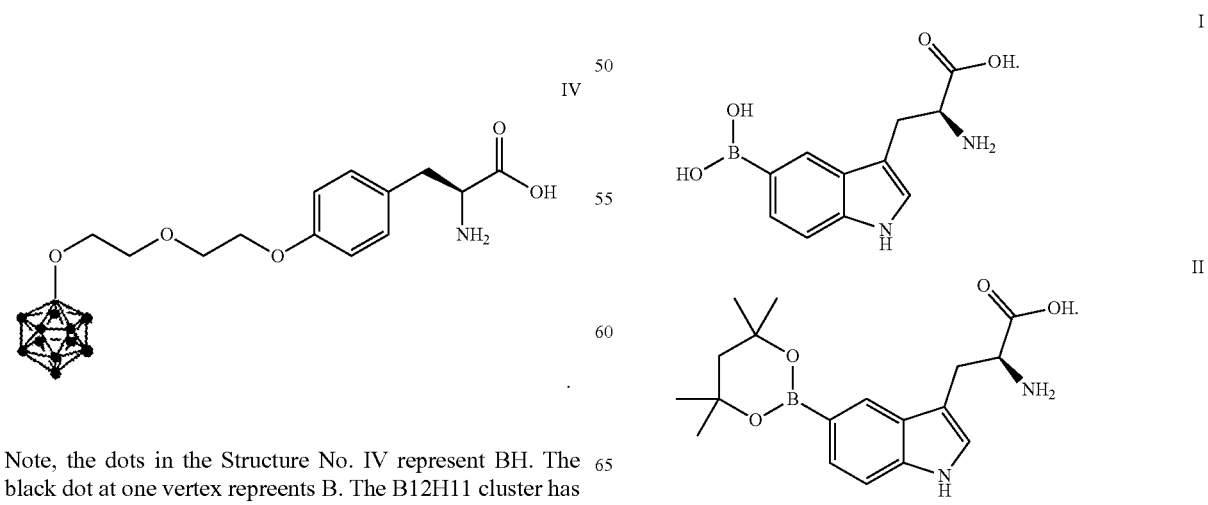

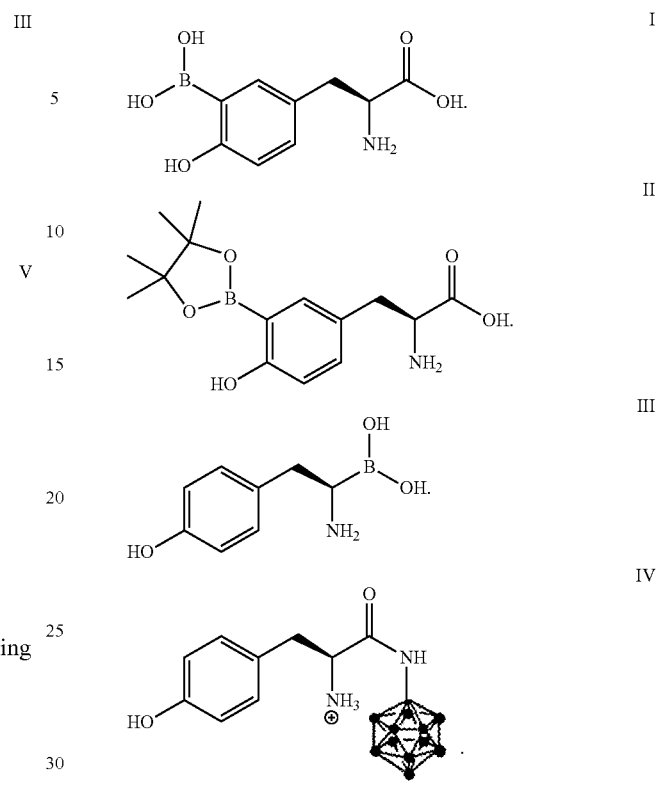

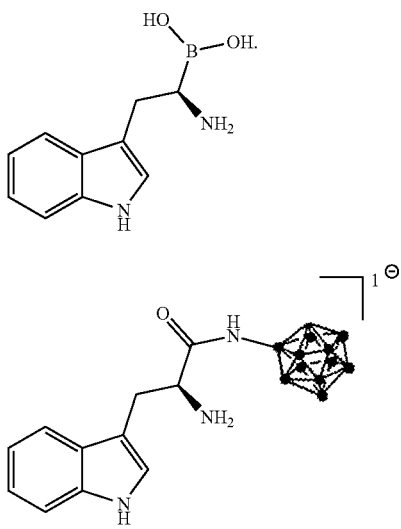

(f) BAA Comprisng Tyrosine

Tyrosine is an essential amino acid with the following chemical formula:

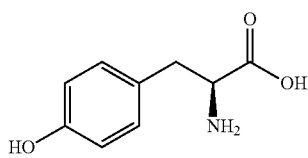 [SMILES: N[C@@H](Cc1ccc(O)cc1)C(=O)O]

and is known to readily pass the blood-brain barrier. Once in the brain, it is a precursor for the neurotransmitters dopamine, norepinephrine and epinephrine, better known as adrenalin. These neurotransmitters are an important part of the body's sympathetic nervous system, and their concentrations in the body and brain are directly dependent upon dietary tyrosine. Tyrosine is rapidly metabolized. Folic acid, copper and vitamin C are cofactor nutrients of these reactions. Tyrosine is also the precursor for hormones, thyroid, catecholestrogens and the major human pigment, melanin. Tyrosine is an important amino acid in many proteins, peptides and even enkephalins, the body's natural pain reliever. Valine and other branched amino acids, and possibly tryptophan and phenylalanine may reduce tyrosine absorption. A number of genetic errors of tyrosine metabolism occur, such as hawkinsinuria and tyrosinemia I. Most common is the increased amount of tyrosine in the blood of premature infants, which is marked by decreased motor activity, lethargy and poor feeding. Infection and intellectual deficits may occur. Some adults also develop elevated tyrosine in their blood. This indicates a need for more vitamin C. Generally speaking tyrosine is needed under stress, and tyrosine supplements prevent the stress-induced depletion of norepinephrine and may cure biochemical depression.

Accordingly, the utilization of borylated tyrosine as a neutron capture agent in certain cancers is contemplated by the present disclosure.

In one embodiment of the present disclosure, a BAA comprising tyrosine has the following chemical formula:

(g) BAA Comprising Histidine

Histidine is an alpha-amino acid with an imidazole functional group with the following chemical formula:

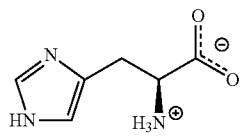

It is one of the twenty-two (22) proteinogenic amino acids. Histidine is an essential amino acid in humans and other mammals. Histidine is a precursor for histamine and carnosine biosynthesis. Inborn errors of histidine metabolism, including histidinemia, maple syrup urine disease, propionic acidemia, and tyrosinemia I, exist and are marked by increased histidine levels in the blood. Elevated blood histidine is accompanied by a wide range of symptoms, from mental and physical retardation to poor intellectual functioning, emotional instability, tremor, ataxia and psychosis. Histidine and other imidazole compounds have anti-oxidant, anti-inflammatory and anti-secretory properties. The efficacy of L-histidine in protecting inflamed tissue is attributed to the capacity of the imidazole ring to scavenge reactive oxygen species (ROS) generated by cells during acute inflammatory response. Histidine, when administered in therapeutic quantities is able to inhibit cytokines and growth factors involved in cell and tissue damage (See, U.S. Pat. No. 6,150,392, THOMES, et. al.). Histidine in medical therapies has its most promising trials in rheumatoid arthritis where up to 4.5 g daily have been used effectively in severely affected patients. Arthritis patients have been found to have low serum histidine levels, apparently because of very rapid removal of histidine from their blood. Other patients besides arthritis patients that have been found to be low in serum histidine are those with chronic renal failure. Urinary levels of histidine are reduced in pediatric patients with pneumonia. Asthma patients exhibit increased serum levels of histidine over normal controls. Serum histidine levels are lower and are negatively associated with inflammation and oxidative stress in obese women. Histidine supplementation has been shown to reduce insulin resistance, reduce BMI and fat mass and suppress inflammation and oxidative stress in obese women with metabolic syndrome. Histidine appears to suppress pro-inflammatory cytokine expression, possibly via the NF-κB pathway, in adipocytes. Low plasma concentrations of histidine are associated with protein-energy wasting, inflammation, oxidative stress, and greater mortality in chronic kidney disease patients. Histidine may have many other possible functions because it is the precursor of the ubiquitous neurohormone-neurotransmitter histamine. Histidine increases histamine in the blood and potentially in the brain. Low blood histamine with low serum histidine occurs in rheumatoid arthritis patients. Low blood histamine also occurs in some manic, schizophrenic, high copper and hyperactive groups of psychiatric patients.

Accordingly, the utilization of borylated histidine as a neutron capture agent in certain cancers is contemplated by the present disclosure.

In one embodiment of the present disclosure, a BAA comprising histidine has the following chemical formula:

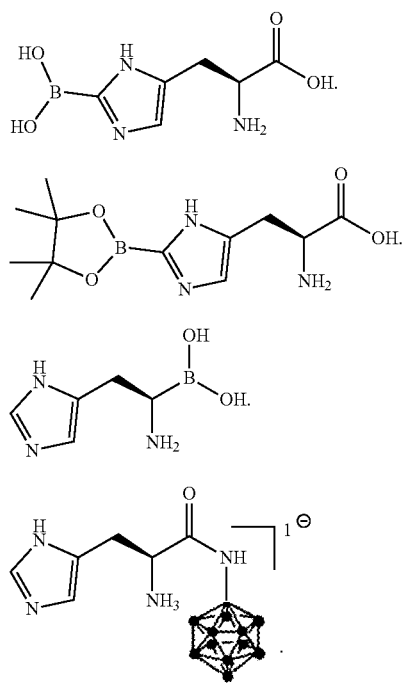

VII.) Boron Neutron Capture Therapy Using BAAs

One aspect of the present disclosure is the use of BAAs as a modality for Boron Neutron Capture Therapy (BNCT) and/or Boron Proton Capture Therapy ("BPCT"). Briefly, BNCT is a binary treatment modality in which neither component alone is lethal or toxic to the tumor. The two components comprise (i) the infusion or delivery of a capture compound, which preferentially is concentrated in the tumor, and (ii) the irradiation of the tumor site by neutrons or by protons In BNCT, given the large cross-section of thermal neutron interactions with $^{10}B$, there is consequently a high probability of a splitting of Boron nucleus into $^{4}He^{2+}$ and $^{7}Li^{+}$. Given that the ionization capability of $He^{2+}$ and $Li^{+}$ is high, and the distances travelled are short, then the cells preferably enriched by Boron are killed and the healthy cells are damaged much less due to the lack of high concentration of boron. Given this, the advantage of BNCT is the destruction of tumor cells without a highly traumatic surgical procedure. However, as will be understood by one of skill in the art, success is predicated high concentration and selective localization of $^{10}B$ in tumor cells.

In one embodiment, $^{10}B$ is concentrated on a BAA. The BAA is then given to a patient and the BAA is localized into a tumor cell. The BAA containing $^{10}B$ are concentrated into the tumor and the tumor is irradiated using epithermal neutrons. The tumor cells are destroyed.

VIII. Proton Boron Fusion Therapy using BAAs

Another apect of the present disclosure is the use of BAAs as a modality for Proton Boron Fusion Therapy (PBFT). Briefly, the proton boron fusion reaction was introduced in the 1960s. Three alpha particles are emitted after the reaction between a proton ($^{1}H$) and a boron particle ($^{11}B$). These three alpha particles provide the damage to the tumor cell, just as in the case of alpha particles in BNCT. Theoretically, in the case of PBFT, the therapy efficacy per incident particle is three times (3×) greater than that of BNCT. In addition, because the proton beam has the advantage of a Bragg-peak characteristic, normal tissue damage can be reduced. Generally speaking many studies for tumor treatment using alpha particles have been performed. In order to take advantage of alpha particles for dose delivery, two key points should be considered. First, the boron uptake should be labeled accurately to the target cell. As mentioned previously, alpha particles are generated where the boronate compound is accumulated. If this happens in normal tissue near the tumor region, alpha particles will damage the normal tissue as well as the tumor cell. Second, the number of generated alpha particles is also a significant factor for effective therapy. By using PBFT, a more effective therapy can be realized compared to BNCT or conventional proton therapy alone.

In one embodiment, $^{10}B$ and/or $^{11}B$ is concentrated on a BAA. The BAA is then given to a patient and the BAA is localized into a tumor cell. The BAA containing $^{10}B$ and/or $^{11}B$ are concentrated into the tumor and the tumor is irradiated using epithermal neutrons. The tumor cells are destroyed.

IX. Methods of Delivering BAAs to a Cell

As will be appreciated by one of ordinary skill in the art, the ability to efficiently deliver high concentrations of Boron to a cell is an advantage of the present invention.

It is shown that the BAAs of the present disclosure enables a higher amount of boron to be administered to a cell safely in mammals. Briefly, BAAs of the disclosure are prepared as set forth in the disclosure. The resulting BAA are taken up by the tumor cell by the upregulated LAT-1 transporter protein.

X.) Kits/Articles of Manufacture

For use in the laboratory, prognostic, prophylactic, diagnostic and therapeutic, applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a BAA or several BAAs of the disclosure. Kits can comprise a container comprising a drug unit. The kit can include all or part of the BAAs and/or diagnostic assays for detecting cancer and/or other immunological disorders.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as BAAs of the disclosure. The article of manufacture typically comprises at least one container and at least one label. Suitable containers include, for example, bottles, vials, syringes, and test tubes. The containers can be formed from a variety of materials such as glass, metal or plastic. The container can hold one or several BAAs and/or one or more therapeutics doses of BAAs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a BAA of the present disclosure.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1: Synthesis of BAA No. 1 Comprising Phenylalanine

BAA No. 1 comprising Phenylalanine is synthesized in the following manner. The protected BPA will be subjected to decarboxylation-borylation, followed by deprotection to reveal the target material.

BAA No. 1 comprising phenylalanine has the following chemical structure:

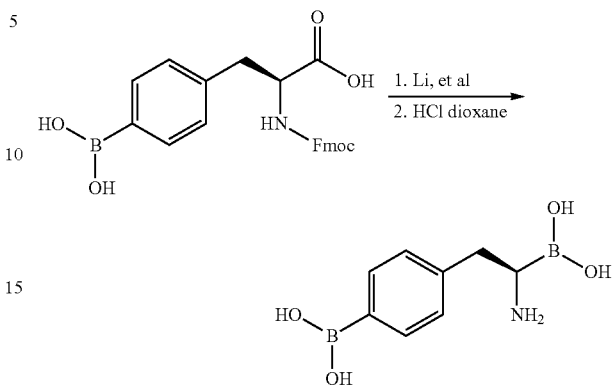

Example 2: Synthesis of BAA No. 2 Comprising Histidine

BAA No. 2 comprising histidine is synthesized in the following manner. The protected histidine will be subjected to decarboxylation-borylation, followed by deprotection to reviel the target material.

BAA No. 2 comprising hisitdine has the following chemical structure:

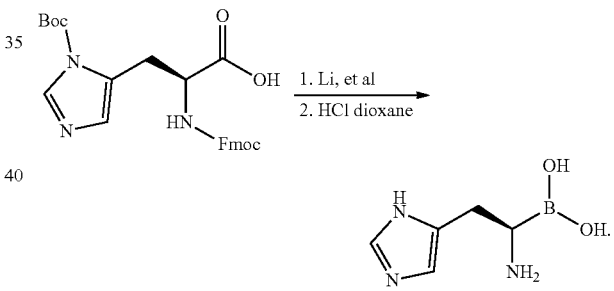

Example 3: Synthesis of BAA No. 3 Comprising Histidine

BAA No. 3 comprising histidine is synthesized in the following manner. The protected histidine succinate will be subjected to nucleophylic addition by BNH, followed by deprotection to reviel the target material.

BAA No. 3 comprising hisitdine has the following chemical structure:

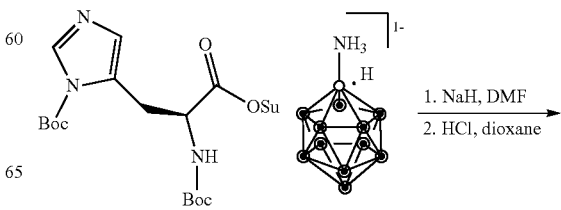

-continued

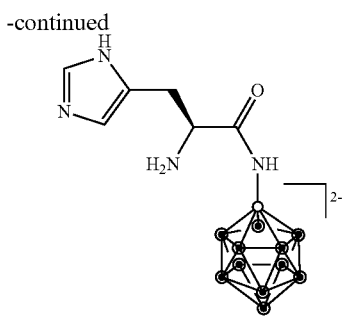

Example 4: Synthesis of BAA No. 4 Comprising Histidine

BAA No. 4 comprising histidine is synthesized in the following manner. The protected histidine will be subjected to organo-lithiation, followed by addition into trimethylborate, and then deprotection to reviel the target material.

BAA No. 4 comprising hisitdine has the following chemical structure:

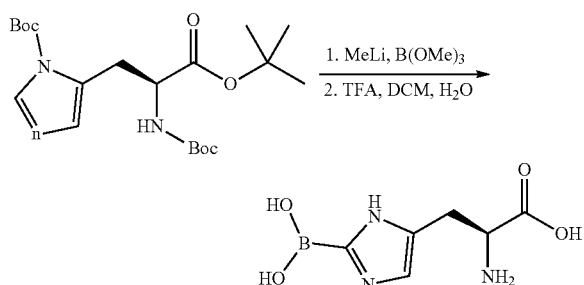

Example 5: Synthesis of TLS00192

The BAA compound known as TLS00192 was synthesized using the following protocol (See, FIG. 3). First, To a solution of tyrosine methyl ester in dichloromethane is added triethylamine followed by di-tert-butyl dicarbonate. Following completion of the reaction, unreacted starting material is removed in an acidic wash, the solvent is then removed under reduced pressure.

Then, isolated boc-tyrosine methyl ester was added to a solution of DMF and potassium carbonate, then was added methyl iodide. Upon completion the reaction, it was diluted with water and extracted into ethyl acetate, the organic layer was washed with saturated aqueous NaCl, and dried over anhydrous sodium sulfate.

Then, to a mixture of iodine and silver sulfate in methanol was added the protected tyrosine compound. Upon completion of the reaction a precipitate was removed by filtration. The filtrate was washed with 10% aqueous sodium bisulfite solution, then water. After drying over anhydrous sodium sulfate, the solvent was removed under reduced pressure. The product was isolated via column chromatography on silica gel.

Then, in DMSO was added the catalyst $Pd(dppf)Cl_2$, bis(pinacolato)diboron, and potassium acetate, then the system was flushed with nitrogen. A solution of iodo-tyrosine in DMSO was then added to the reaction, and the temperature was brought to 80° C. The product was extracted into ethyl acetate with water washes, dried over magnesium sulfate, and following filtration the solvent was removed under reduced pressure.

Then, the pinacole boronated tyrosine was solubilized in acetone, to which was added $NaIO_4$. After stirring the reaction mixture for fifteen (15) min. one (1) M HCl was added, and the reaction was allowed to stir for four (4) hr. The resulting mixture was extracted with EtOAc, washed with deionized water, and finally washed with brine. The organic layer was dried over $MgSO_4$. After filtering, the organic solvent was removed under vacuum.

Then, a solution of the aforementioned synthesized boronic acid methyl ether tyrosine in DCM was brought to −78° C., and flushed with nitrogen. To this mixture was added boron tribromide dropwise, and allowed to react for twelve (12) hr. The reaction was poured into water and extracted, dried over magnesium sulfate, and subsequent removal of the solvent under vacuum.

Finally, the boronic acid tyrosine methyl ester was put in a three (3) to one (1) solution of THF to water. To this was added LiOH, and allowed to react until only target material was observed. The solution was neutralized with HCl and the solvent removed under reduced pressure.

TLS00192 has the following chemical structure:

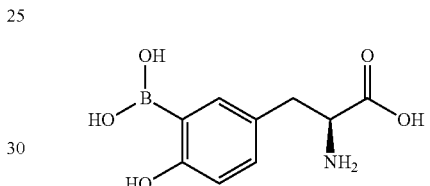

Example 6: Synthesis of TLS00178

The BAA compound known as TLS00178 was synthesized using the following protocol (See, FIG. 4). First, at 0° C. to a solution of DMF is added 1-ammine-undecahydro-dodecaborate, then sodium hydride is added portion-wise. Once gas evolution has ceased the succinimide ester of boc-protected histidine is added. After concentration the material is telescoped forward. Four (4) molar HCl in dioxane is added to the material, as well 12% by volume of water is added. Once the reaction has fully converted, as monitored by LCMS, the solvents are removed under reduced pressure. The target material is obtained by trituration with ethanol.

TLS00178 has the following chemical structure:

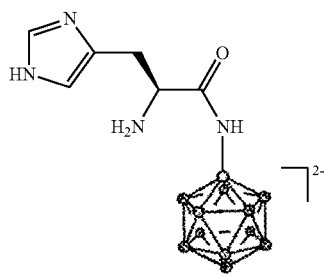

Example 7: Synthesis of TLS00190

The BAA compound known as TLS00190 was synthesized using the following protocol (See, FIG. 5). First, At 50° C. to a solution of acetonitrile/water, 20% v/v, is added the boc-protected methyl ester of tyrosine. To this solution is then added potassium carbonate and allowed to react for fifteen (15) minutes. 1-(1,4-dioxane)-undecahydrododecaborate. The reaction is allowed to proceed overnight. The solvent is exchanged to MeOH/water, 20% v/v. Lithium hydroxide is added and the solution is brought to reflux. Once no methyl ester is observed the reaction is neutralized with HCl and the solvent is removed. The material is brought up in four (4) molar HCl in dioxane, to which 20% v/v of water is added. Target material is obtained via preparative liquid chromatography.

TLS00190 has the following chemical structure:

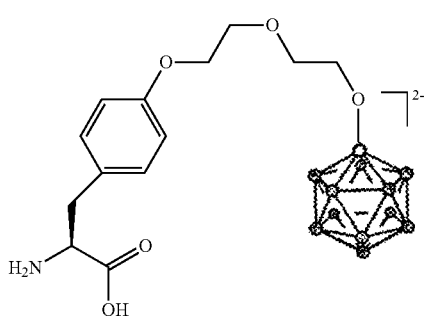 [SMILES: COCCOCCOc1ccc(C[C@H](N)C(=O)O)cc1]

Example 8: LCMS Purity and Mass Confirmation of TLS00192, TLS00178, and TLS00190

LS/MS Purity confirmation of TLS00192, TLS00178, and TLS00190 was carried out by LCMS. Briefly, an LCMS using Acquity H-class system (Waters, Miford, MA) equipped with either Acquity BEH C18 column (50×2.1 mm, 1.7 μm) or C18 Peptide CSH column (100×2.1 mm, 1.7 μm) maintained at 40° or 60° C. in the gradient of acetonitrile mobile phase containing 0.1% formic acid. The detection was carried out using QDA ESI mass spectrometer.

The results in FIG. 6-8, show HPLC UV traces showing purity and mass confirmation of TLS00192 (FIG. 6); TLS00178 (FIG. 7) and TLS00190 (FIG. 8). All the compounds were produced in the purity meeting or exceeding 90%; the MS ionization mode was optimized for each compound. In addition, a summary of the purity and mass confirmation of TLS00192, TLS00178, and TLS00190 is set forth in FIG. 9.

Example 9: Kinetic Parameters of TLS00192 and BPA-Fructose

To investigate the ability of TLS00192 to deliver boron to FaDu nasopharnygeal squamous carcinoma cells, we interrogated a range of concentrations bracketing what is hypothsized to be physiologically relevant amounts for boronophenylalanine (BPA), currently the most widely studied boron drug in BNCT clinical practice.

The FaDu cell line is a human nasopharyngeal carcinoma cell line. The cell line was obtained from the American Type Culture Collection ("ATCC"), located at 10801 University Boulevard Manassas, VA 20110-2209 USA in 2019. It has ATCC designation of HTB-43™ and lot number 70014320. FaDu cells are propagated in DMEM culture medium supplemented with 10% fetal bovine serum with routine passage by trypsinization and reseeding. The cell line is cryopreserved in liquid nitrogen.

Additionally, boron measurement was performed by ICP OES. on an Agilent 5110 ICP-OES. The data was analyzed using Agilent's ICP Expert Software, version 7.4.2.10790. Boron was measured axially at the 249.772 nm wavelength and the internal standard Beryllium was measured axially at the 313.042 nm wavelength. Beryllium internal standard was spiked into the solution at 1:5 the flowrate before introduction to the spray chamber via a T-connector. Finally, A standard curve using 1000, 100, 10, 1 and 0 ppb of boron was used to calculate the concentration of boron in each sample.

To determine the kinetic parameters of TLS00192, Boron compounds were added to FaDu cells at the final concentration of 2.5 mM in HBSS and the cells were incubated at 37° C., in a humidified 5% $CO_2$ atmosphere for two (2) hrs with shaking. Following two (2) hour incubation, cells were harvested and suspended in ice cold PBS and lysed in RIPA buffer and protein content determined by BCA assay. A portion was also subjected to boron measurements using ICP-OES. Results were expressed as ng boron/per mg cell protein/per minute. Kinetic parameters, Velocity and Km, were determined by Michaelis-Menton non-linear regression using Prism (GraphPad) software.

The results show that uptake saturation was reached at substrate concentrations exceeding 5 mM and reaching a plateau at approximately 10 mM. Both TLS00192 and BPA-fructose compounds exhibited concentration dependent cellular uptake that was efficient and saturable following typical Michaelis-Menten kinetics. A Michaelis Menton non-linear regression curve fit indicated that the Km for TLS00192 is approximately 50% of that for BPA-fructose (1.97 mM vs. 0.84 mM, respectively) suggesting that BPA may be a preferred LAT-1 substrate. (FIG. 10).

It is noted that the data is consistent with the data reported for non-borylated amino acids. See, KANAI, et al. J. Biol. Chem. 1998, 273, 23629-23632. However, the apparent Vmax for TLS00192 is higher (8.91 vs 15.87 ng boron $mg^{-1}$ $min^{-1}$). The higher rate of boron accumulation into the cell line for TLS00192 indicates either (i) higher uptake rate or (ii) slower efflux (i.e. better retention of TLS00192 compared to BPA-fructose).

Example 10: Cellular Retention of TLS00192 and BPA-Fructose in FaDu Cells

Subsequently, to determine whether the efflux mediated by either LAT1 or LAT2 or other transporters is equal for BPA-fructose relative to TLS00192 in cellular retention tests in FaDu cells. The "time zero" sample was immediately harvested following an initial two (2) hour incubation with the compounds. Cells were then harvested at indicated times and subjected to lysis, boron measurement, and protein content. Data is expressed as % residual boron content of time zero amount.

The results in FIG. 11 show gradual elimination of boron from the cells at both time points. However, TLS00192 elimination is much slower compared to BPA-fructose. It is noted that by sixteen (16) hours there is greater than 40% of residual TLS00192 compared to approximately 10% of residual BPA. These results indicate a distinctive feature of TLS00192 compared to BPA that improves the amount of boron delivered to cells.

Example 11: LAT-1 Mediated Competition Studies for TLS00192

It has been shown that the system L transporter (LAT-1) mediates the transport of L-amino acids into cells and plays a major role in the uptake of BPA in BPA-based BNCT (WONGTHAI, et. al. Cancer Sci Vol. 106, pg. 279-286, 2015). To assess whether TLS00192 is transported via LAT-1 dependent mechanism we interrogated its ability to be outcompeted by the LAT1 substrate L-Phe FaDu cells were incubated in HBSS medium for two (2) hours at 37° C. with 0.5 mM of either TLS00192 or BPA-fructose in the absence (Subset A) or presence of increasing concentrations of competitor Phe (Subset B), L-system antagonist BCH (Subset C) or LAT-1 specific inhibitor JPH203 (Subset D). The cells were harvested, and the amount of each boronated cell associated compound was determined by ICP OES. The IC50s for the respective inhibitor on each compound is also indicated. BPA was used as a positive control for LAT-1-mediated uptake.

As you can see, the results in FIG. 12A show the uptake of the pure compounds in the absence of a competitor. For this and subsequent studies TLS00192 was maintained at 0.5 mM. Increased concentrations of Phe in the range of 0.01 to 20 mM exhibited reduction in the uptake for both BPA and TLS00192 (See, FIG. 12B). It is notable an unexpected result that approximately one log higher concentration of L-Phe competitor was required to inhibit TLS00192 LAT1-mediated transport. The IC50 was 0.04 and 0.43 mM for L-Phe in the presence of BPA-Fructose and TLS00192, respectively. As a result, it is shown that TLS00192 is able to more successfully compete with endogenous amino acids and utilize effectively LAT-1 to gain cellular accumulation compared to BPA.

Next, evaluation of pan-LAT antagonist 2-aminobicyclo-(2,2,1)-heptane-2-carboxylic acid (BCH) (FIG. 12C) and a specific LAT-1 inhibitor JPH203 (FIG. 120) in the competition assay was performed. Similar to the results in FIG. 12B, BCH inhibited boron uptake in a concentration-dependent manner. BPA was more easily competed by BCH as compared to TLS00192 (0.14 and 0.80 mM for BPA and TLS00192, respectively). JPH203 was an even stronger inhibitor of LAT1-mediated uptake of TLS00192 and BPA than BCH e.g. 0.19 and 0.78 μM, respectively (FIG. 12D). The results show that (i) the TLS00192 uptake is LAT-1 mediated and (ii) it takes higher concentration of a competitor to displace TLS00192 from the LAT-1 binding pocket.

Example 12: Boron Uptake of TLS00190 and TLS00178 in FaDu Cells

The efficiency of boron uptake of TLS00190 and TLS00178 was determined using FaDu cells. Following a two (2) hour incubation, cells were harvested and suspended in ice cold PBS and a portion was lysed in RIPA buffer and protein content determined by BCA assay. The remaining portion was subjected to boron measurements were carried out using ICP-OES. BPA-fructose was used as a control. After two (2) hours of incubation the amount of the compounds taken up was determined based on the boron measurements.

The results, as expressed as ng boron per mg protein, are shown in FIG. 13. The TLS00190 has a $B_{12}H_{11}^{2-}$ boron cluster linked to the phenylalanine side chain. TLS00178 has a $B_{12}H_{11}^{2-}$ boron cluster linked to the C-terminus of histidine. As is shown, both of these compounds modfied with a 12 boron cluster either on their respective side chains or on the C-terminus, retain the ability to be transported into FaDu cancer cells.

In addition, the retention of TLS00190 and TLS00178 following initial 2 hour uptake compared to BPA-Fructose was also studied in FaDu cells. As shown in FIG. 14, BPA-Fructose was eliminated from cells to a level of approximately 8% at twenty (20) hrs. similar to what was seen before, however TLS00190 and TLS00178 were retained at levels of 43% and 57%. Notably, TLS00190 cellular levels dropped to levels of 14% at two (2) hours, but rose back up to 43% at twenty (20) hours, suggesting the ability to re-accumulate back into cells following excretion. These characteristics of TLS00190 and TLS0078 suggest the potential for better accumulation and retention in cancer cells of BNCT patients compared to BPA-Fructose.

Example 13: Human Clinical Trials for the Treatment of Human Carcinomas Through the Use of BAAs BAAs are synthesized in accordance with the present invention which specifically accumulate in a tumor cell, and are used in the treatment of certain tumors and other immunological disorders and/or other diseases. In connection with each of these indications, two clinical approaches are successfully pursued.

I.) Adjunctive therapy: In adjunctive therapy, patients are treated with BAAs in combination with a chemotherapeutic or pharmaceutical or biopharmaceutical agent or a combination thereof. Primary cancer targets, are treated under standard protocols by the addition of BAAs and then irradiated. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the BAAs in monotherapy of tumors, the BAAs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of-standard chemotherapy and other biologic agents.

Dosage

Dosage regimens may be, adjusted to provide the optimum desired response. For example, a single BAA injection may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the BAA, the individual mechanics of the irradiation mechanism (reactor) and the particular therapeutic or prophylactic effect to be achieved, and (b) the limitations inherent in the art of compounding such an compound for the treatment of sensitivity in individuals.

Clinical Development Plan (CDP)

The CDP follows and develops treatments of cancer(s) and/or immunologica disorders using BAAs of the disclosure which are then irradiated using Neutron Capture Therapy in connection with adjunctive therapy or monotherapy. Trials initially demonstrate safety and thereafter confirm efficacy in repeat doses. Trials are open label comparing standard chemotherapy with standard therapy plus BAAs which are then irradiated using Boron Neutron Capture Therapy. As will be appreciated, one non-limiting criteria that can be utilized in connection with enrollment of patients is concentration of BAAs in a tumor as determined by standard detection methods known in the art.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Naturally Occuring Amino Acids.

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

The invention claimed is:

1. A method of delivering a borylated amino acid composition to a cell for treating a disease, the method comprising:
(i) administering to a patient a Dosage Unit Form composition comprising a chemical structure as follow:

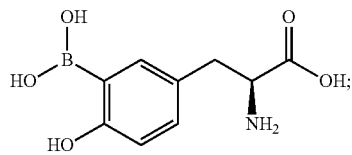 [SMILES: N[C@@H](Cc1ccc(O)c(B(O)O)c1)C(=O)O]

(ii) allowing the Dosage Unit Form composition to accumulate in the cell; and
(iii) irradiating the cell with neutrons.

2. The method of claim 1, wherein the patient is a human.

3. The method of claim 1, wherein the Dosage Unit Form is accumulated into the cell by the LAT-1 amino acid transporter.

4. The method of claim 1, wherein the treatment is Boron Neutron Capture Therapy (BNCT).

5. The method of clam 1, wherein the treatment is Proton Boron Fusion Therapy (PBFT).

6. The treatment of claim 4, wherein the BNCT is used to treat head and neck cancer, glioblastoma and melanoma.

7. The treatment of claim 5, wherein the PBFT is used to treat head and neck cancer, glioblastoma and melanoma.

8. A composition comprising a chemical structure as follows:

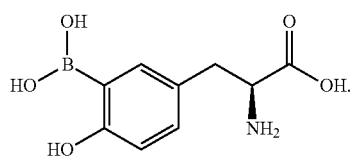 [SMILES: N[C@@H](Cc1ccc(O)c(B(O)O)c1)C(=O)O]

9. A Dosage Unit Form comprising a composition of claim 8.

10. The Dosage Unit Form of claim 9, wherein the Dosage Unit Form is used in Boron Neutron Capture Therapy (BNCT).

11. The Dosage Unit Form of claim 10, wherein the BNCT is used to treat head and neck cancer, glioblastoma and melanoma.

* * * * *